United States Patent
Huang

(10) Patent No.: US 9,074,051 B2
(45) Date of Patent: Jul. 7, 2015

(54) DIANHYDRIDE MONOMER HAVING SIDE CHAIN, POLYIMIDE COMPOUND HAVING SIDE CHAIN AND MANUFACTURING METHOD THEREOF

(71) Applicant: UNIMICRON TECHNOLOGY CORP., Taoyuan Hsien (TW)

(72) Inventor: Han-Pei Huang, Taoyuan County (TW)

(73) Assignee: Unimicron Technology Corp., Taoyuan County (TW)

( * ) Notice: Subject to any disclaimer, the term of this patent is extended or adjusted under 35 U.S.C. 154(b) by 156 days.

(21) Appl. No.: 13/845,311

(22) Filed: Mar. 18, 2013

(65) Prior Publication Data

US 2014/0275470 A1    Sep. 18, 2014

(51) Int. Cl.
*C08G 73/10* (2006.01)
*C07D 407/12* (2006.01)

(52) U.S. Cl.
CPC .......... *C08G 73/1053* (2013.01); *C07D 407/12* (2013.01); *C08G 73/10* (2013.01)

(58) Field of Classification Search
CPC ............................ C08G 73/10; C08G 73/1053
USPC .......................................... 528/271, 310, 332
See application file for complete search history.

(56) References Cited

U.S. PATENT DOCUMENTS

| | | | |
|---|---|---|---|
| 3,956,320 A * | 5/1976 | Heath et al. | 549/241 |
| 6,060,575 A | 5/2000 | Yang et al. | |
| 2011/0263791 A1* | 10/2011 | Chiong et al. | 525/132 |

FOREIGN PATENT DOCUMENTS

| | | | |
|---|---|---|---|
| CN | 101704807 A | | 5/2010 |
| CN | 102504295 | * | 6/2012 |

OTHER PUBLICATIONS

Hsiao, et al.; "Synthesis and Properties of Poly(ether Imide)s Derived from 2,5-Bis(3,4-Dicarboxyphenoxy)biphenyl Dianhydride and Aromatic Ether—Diamines"; Journal of Applied Polymer Science, vol. 113, 3993-4002 (2009).

Hsiao, et al.; "Synthesis and Properties of Poly(ether imide)s Based on the Bis(ether anhydride)s from Hydroquinone and Its Derivatives"; Journal of Polymer Science: Part A: Polymer Chemistry, vol. 37, 665-675 (1999).

* cited by examiner

*Primary Examiner* — Gregory Listvoyb
(74) *Attorney, Agent, or Firm* — Rosenberg, Klein & Lee

(57) ABSTRACT

A dianhydride monomer having a large side chain R is provided. The large side chain would interrupt the symmetry and regularity of diamine monomer. The diamine monomer has the general formula shown as formula (I) below:

formula (I)

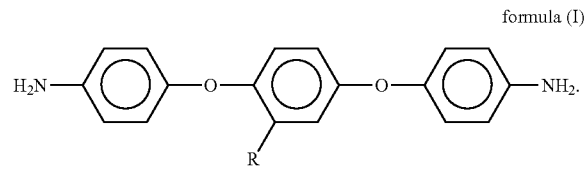

The functional group R includes α-substitution cycloalkene having at least a tertiary carbon atom, cycloalkene having at least a tertiary carbon atom, cycloalkane having at least a tertiary carbon atom, α-substitution phenyl, phenyl, α-substitution naphthalyl, naphthalyl, α-substitution phenanthrenyl, phenanthrenyl, α-substitution anthracenyl, anthracenyl, α-substitution adamantyl, adamantyl, α-substitution adamantyl and adamantyl.

10 Claims, No Drawings

DIANHYDRIDE MONOMER HAVING SIDE CHAIN, POLYIMIDE COMPOUND HAVING SIDE CHAIN AND MANUFACTURING METHOD THEREOF

BACKGROUND

1. Technical Field

The invention relates to dianhydride monomer, polyimide compound and the manufacturing method thereof, and in particular, to dianhydride monomer having side chain, polyimide compound having side chain and the manufacturing method thereof.

2. Description of Related Art

The polyimide is a common engineering plastic with well mechanical property, higher glass transition temperature, and higher thermal degradation temperature. Therefore, polyimide is widely implemented in the semiconductor industry, the photoelectrical industry, and the mechanical industry. Nevertheless, polyimide is hard to dissolve in various kinds of the organic solvents, thus the machinability of polyimide is decreased. So far, several experimental reports about modifying the property of polyimide are published, and those researches are intended to increase the solubility of polyimide while the thermal property can be maintained at the same time.

SUMMARY

The present invention provides dianhydride monomer having a side chain.

The present invention provides a manufacturing method for dianhydride monomer.

The present invention provides polyimide compound having a side chain.

The present invention provides a manufacturing method for polyimide compound.

The present invention provides dianhydride monomer having the side chain. The side chain of dianhydride monomer can decrease the symmetry of dianhydride monomer in structure, and the regularity of dianhydride monomer in molecular arrangement. The above-mentioned side chain is selected from the group consisting of: α-substitution cycloalkene having at least a tertiary carbon atom, a cycloalkane having at least a tertiary carbon atom, cycloalkene having at least a tertiary carbon atom, phenyl, α-substitution phenyl, naphthalyl, α-substitution naphthalyl, anthracenyl, α-substitution anthracenyl, phenanthrenyl, α-substitution phenanthrenyl, aromatic hydrocarbons, α-substitution aromatic hydrocarbons, adamantyl, α-substitution adamantyl, adamantyl, and α-substitution adamantyl.

The present invention provides a manufacturing method for dianhydride monomer. The method comprising: (A) The solution containing the bromo compound, the hydroquinone compound, and the benzene is heating refluxed for distillation. The solid hydroquinone compound is separated out in the distillation. (B) The solution containing hydroquinone compound and 4-nitrophthalonitrile is heated. The methanol as the precipitant is added into the above-mentioned solution to from the bis(3,4-dicyanophenoxy) compound. (C) The solution containing bis(3,4-dicyanophenoxy) compound, potassium hydroxide (KOH), and methanol are heating refluxed. The solid bis(3,4-dicarboxyphenoxy) compound is separated out. (D) The dehydrated ring-closure of the solution containing bis(3,4-dicarboxyphenoxy) compound, acetic anhydride, and anhydrous acetic acid anhydride is carried out to from the dianhydride monomer.

The present invention provides polyimide compound having the side chain. The polyimide compound is made of the above-mention dianhydride monomer. The side chain of the polyimide compound interrupts the symmetry of polyimide compound in structure, and the regularity of polyimide compound in molecular arrangement. The above-mentioned side chain is selected from the group consisting of: α-substitution cycloalkene having at least a tertiary carbon atom, a cycloalkane having at least a tertiary carbon atom, cycloalkene having at least a tertiary carbon atom, phenyl, α-substitution phenyl, naphthalyl, α-substitution naphthalyl, anthracenyl, α-substitution anthracenyl, phenanthrenyl, α-substitution phenanthrenyl, α-substitution aromatic hydrocarbons, aromatic hydrocarbons, adamantyl, α-substitution adamantyl, adamantyl, α-substitution adamantyl.

The present invention provides a manufacturing method for polyimide compound. The method comprising: (A) Under anhydrous condition, dianhydride monomer and diamine monomer are dissolved into cresol by stirring to from polyamic acid compound solution. (B) The 5-10 drops of isoquinoline are added to the polyamic acid compound solution. The solution containing polyamic acid compound solution and isoquinoline is heating refluxed to form polyimide compound solution. (C) The polyimide compound solution is cooled and added to the ethanol. The solid polyimide compound than precipitates out.

To sum up, the present invention provides dianhydride monomer having the side chain, polyimide compound having the side chain, and the manufacturing method thereof. The symmetry in structure and the regularity in molecular arrangement of above-mention dianhydride monomer having large side chain is interrupted. Thus, the intermolecular force of polyimide compound is attenuated and the solubility of polyimide compound increases.

In order to further appreciate the characteristic and technical contents of the present invention, references are hereunder made to the detailed descriptions and appended drawings in connection with the present invention. However, the appended drawings are merely shown for exemplary purpose rather than being used to restrict the scope of the present invention.

DESCRIPTION OF THE EXEMPLARY EMBODIMENTS

The present invention provides dianhydride monomer (e) having side chain. The general formula of dianhydride monomer (e) is shown as formula (I):

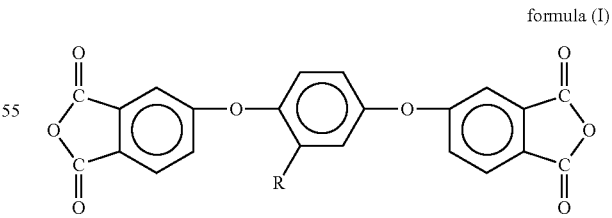

formula (I)

The functional group R is selected from the larger functional group consisting of: α-substitution cycloalkene having at least a tertiary carbon atom, cycloalkane having at least a tertiary carbon atom, cycloalkene having at least a tertiary carbon atom, α-substitution phenyl, phenyl, α-substitution naphthalyl, naphthalyl, α-substitution anthracenyl, anthracenyl, α-substitution phenanthrenyl, phenanthrenyl, α-substitution aromatic hydrocarbons, aromatic hydrocarbons, adamantyl, α-substitution adamantyl, adamantyl, α-substitution adamantyl.

Next, the manufacturing method for above-mention dianhydride monomer (e) is introduced. The manufacturing method comprises four main steps: forming hydroquinone compound (b), forming bis(3,4-dicyanophenoxy) compound (c), forming bis(3,4-dicarboxyphenoxy) compound (d), and forming dianhydride monomer (e). It is worth noting that the "R" mentioned hereafter is one of the larger functional groups listed above and the detailed description of the larger functional groups would be omitted thereafter.

The formation of hydroquinone compound (b) comprises the following steps. Firstly, bromo compound (a), hydroquinone compound, and benzene are added into the reactor in nitrogen ambient. Next, the reactor is heating refluxed for 3-4 days. The reactor might be the three-necked flask. It is worth noting that, nitrogen ambient might prevent the reaction from the influence of the air and the moisture. In addition, the reaction temperature of the heating reflux is at about 80-85° C. as the temperature of benzene boiling point. After the reaction finished, solid hydroquinone compound (b) would be separated out. Solid hydroquinone compound (b) might be obtained directly by the method of filtration. The general formula of bromo compound (a) is shown as formula (II):

formula (II)

The general formula of hydroquinone compound (b) is shown as formula (III):

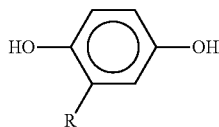

formula (III)

Continued from the preceding paragraph, hydroquinone compound (b) obtained from the method of filtration is washed by the heated water to wash away the excess hydroquinone compound and hydrogen bromide. Hydrogen bromide is the byproduct of the reaction. The temperature of the heated water is about 50-70° C. Next, wet hydroquinone compound (b) is vacuum dried to remove the solvent and the moisture and to obtain solid hydroquinone compound (b). Then, solid hydroquinone compound (b) is recrystallized to enhance the purity of hydroquinone compound (b). The reaction of forming hydroquinone compound (b) is listed as reaction (I):

reaction (I)

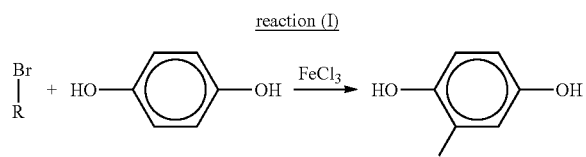

The formation of bis(3,4-dicyanophenoxy) compound (c) comprises the following steps. Firstly, purified hydroquinone compound (b), potassium carbonate ($K_2CO_3$), toluene, and dimethylformamide (DMF) are added into the reactor and heating refluxed for 4 to 5 hours. The hydroquinone compound (b) is dehydrated by the method of azeotrope to from the ionized hydroquinone having the anion. The temperature of azeotrope is at about 150 to 160° C. The general formula of ionized hydroquinone compound (b) is shown as formula (IV):

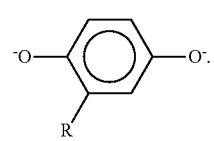

formula (IV)

Continued from the preceding paragraph, next, the solution containing ionized hydroquinone compound (b) and 4-nitrophthalonitrile is heated at 70 to 85° C. for 6 to 12 hours, so as to form bis(3,4-dicyanophenoxy) compound (c) solution. Then, the methanol is utilized as the precipitant to precipitate out solid bis(3,4-dicyanophenoxy) compound (c). Next, solid bis(3,4-dicyanophenoxy) compound (c) is washed by the distilled water, to remove the excess solvent and the reactant. Then, the above-mentioned solution is vacuum dried to obtain the powder bis(3,4-dicyanophenoxy) compound (c). Subsequently, the bis(3,4-dicyanophenoxy) compound (c) is recrystallized to enhance the purity. The general formula of bis(3,4-dicyanophenoxy) compound (c) is shown as formula (V):

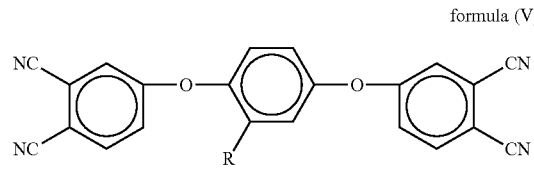

formula (V)

The reaction of forming bis(3,4-dicyanophenoxy) compound (c) is listed as reaction (II):

reaction (II)

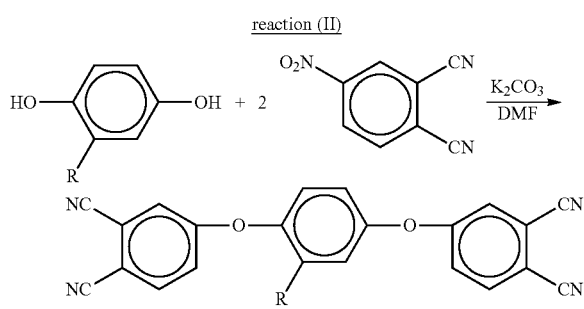

The formation of bis(3,4-dicarboxyphenoxy) compound (d) comprises the following steps. The bis(3,4-dicyanophenoxy) compound (c), potassium hydroxide, and methanol are added to the reactor and heating refluxed for 4 to 5 days. The methanol is taken as the solvent of bis(3,4-dicyanophenoxy) compound (c) and potassium hydroxide. The reaction temperature is about 70 to 85° C. as the temperature of methanol boiling point.

After the reaction, bis(3,4-dicarboxyphenoxy) compound (d) is filtered. Besides, the pH value of the solution of bis(3, 4-dicarboxyphenoxy) compound (d) is adjusted to 2-3 by the hydrogen chloride solution. Therefore, solid bis(3,4-dicarboxyphenoxy) compound (d) is separated out. Subsequently, solid bis(3,4-dicarboxyphenoxy) compound (d) is washed by the distilled water to remove the excess solvent. The general formula of bis(3,4-dicarboxyphenoxy) compound (d) is shown as formula (VI):

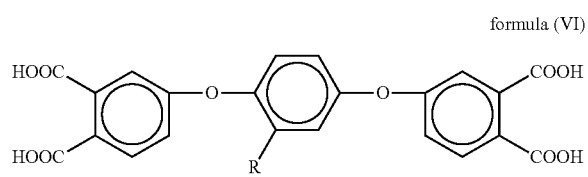

formula (VI)

The reaction of forming bis(3,4-dicarboxyphenoxy) compound (d) is listed as reaction (III):

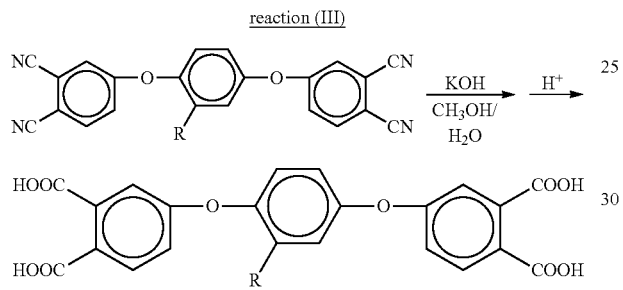

reaction (III)

The formation of dianhydride monomer (e) comprises the following steps. The bis(3,4-dicarboxyphenoxy) compound (d), acetic anhydride, and acetic acid anhydride are added into the reactor and heating refluxed at 130 to 140° C. for 1 to 6 hours. The dehydrated ring-closure of the above-mentioned solution is carried out by the method of heating reflux to form dianhydride monomer (e). The general formula of dianhydride monomer (e) is shown as formula (I):

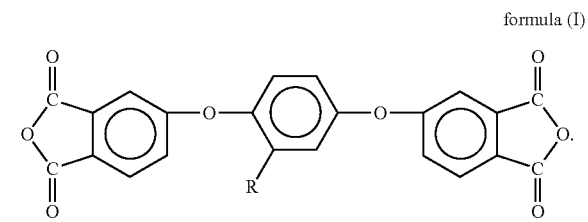

formula (I)

The reaction of forming dianhydride monomer (e) is listed as reaction (IV):

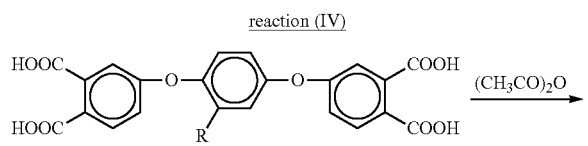

reaction (IV)

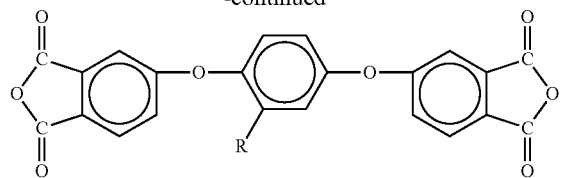

-continued

In the following paragraph, adamantyl is chosen to be the large functional group R of dianhydride monomer (e) in this embodiment. However, the embodiment is merely shown for exemplary purpose rather than being used to restrict the scope of the present invention.

First Embodiment

The dianhydride monomer (e) in the first embodiment of the present invention is 1,4-bis(3,4-dicarboxyphenoxy)-2-adamantyl benzene dianhydride, the formula of the 1,4-bis(3,4-dicarboxyphenoxy)-2-adamantyl benzene dianhydride is shown as formula (VII):

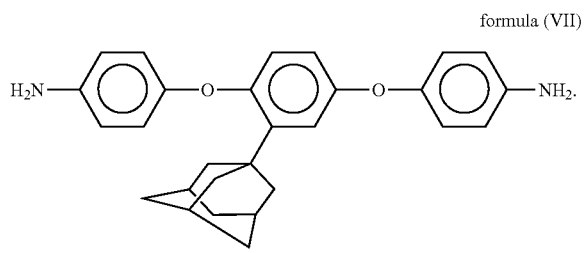

formula (VII)

The formation of the dianhydride monomer comprises the following four steps: forming the 2-adamantyl hydroquinone, forming 1,4-bis(3,4-dicyanophenoxy)-2-adamantyl benzene, forming 1,4-bis(3,4-dicarboxyphenoxy)-2-adamantyl benzene, and forming 1,4-bis(3,4-dicarboxyphenoxy)-2-adamantyl benzene dianhydride.

The formation of the 2-adamantyl hydroquinone comprises the following steps. Firstly, 15 g of 1-bromoadamantane (69.77 mmol), 15.35 g of hydroquinone compound (139.5 mmol), and 75 ml of benzene are added into the 250 ml of the three-necked flask in nitrogen ambient. The solution is heating refluxed for 72 hours. The temperature of the reaction is about 80-85° C. as the temperature of benzene boiling point. It is worth noting that a large amount of white fumes is produced in the process of reaction and the color of the solution would become deeper.

After the reaction, solid 2-adamantyl hydroquinone is separated out and is obtained directly by the method of filtration. After the filtration, solid 2-adamantyl hydroquinone is washed by the heated water to remove the remaining hydroquinone compound. Next, 2-adamantyl hydroquinone is vacuum dried and recrystallized by toluene to enhance the purity of the 2-adamantylhydroquinone. Then, 12.21 g of 2-adamantylhydroquinone is obtained. The appearance of 2-adamantylhydroquinone is yellow transparent needle-like crystal, the yield of 2-adamantylhydroquinone is approximately 71.73%, the melting point (mp) of 2-adamantylhydroquinone is at 217-219° C., and the property of 2-adamantylhydroquinone is listed as below:

IR (KBr) 3437, 3390, 3047, 3015, 2898, 2848, 1597, 1507, 1457 cm-1: MS (EI) m/z 244 (M+, 100), 186 (12).

The formation of 1,4-bis(3,4-dicyanophenoxy)-2-adamantyl benzene comprises the following steps. Firstly, 2 g of 2-adamantyl hydroquinone (8.197 mmol), 1.25 g of anhydrous potassium carbonate (9.06 mmol), 6 ml of toluene, and 40 ml of dimethylformamide are added to the 150 ml of the three-necked flask under the nitrogen ambient. The solution is heating refluxed at 150 to 160° C. for 4-5 hours. The hydroquinone compound (b) is dehydrated by azeotropic of water and toluene to form the ionized hydroquinone having the anion.

Next, 3 g of 4-nitrophtalonitrile (17.34 mmol) is added into the above-mentioned solution to further react at 75 to 80° C. for 12 hours. After the reaction, methanol solution is utilized as the precipitant to precipitate out the pale yellow solid initial product of 1,4-bis(3,4-dicyanophenoxy)-2-adamantyl benzene. Then, bis(3,4-dicyanophenoxy)-2-adamantyl benzene is washed several times by the distilled water and vacuum dried. Next, solid bis(3,4-dicyanophenoxy)-2-adamantyl benzene is recrystallized to enhance the purity. Then, 3.08 g of pale yellow crystal bis(3,4-dicyanophenoxy)-2-adamantyl benzene is obtained with 75.8% of the yield, and approximately 260-261° C. of the melting point. The property of bis(3,4-dicyanophenoxy)-2-adamantyl benzene is listed as below:

IR (KBr) 3078、3039、2922、2851、2236、1601、1564、1480、1421 cm$^{-1}$; MS (EI) m/z 496 (M$^+$, 100), 439 (25).

The formation of 1,4-bis(3,4-dicarboxyphenoxy)-2-adamantyl benzene comprises the following steps. Firstly, 2 g of 1,4-bis(3,4-dicyanophenoxy)-2-adamantyl benzene (4.032 mmol), 5 g of potassium hydroxide (36.2 mmol) are mixed to prepare a solution containing 50% of each respectively. The 50% solution and 100 ml of methanol are added into the 250 ml three-necked flask in nitrogen ambient. Then, the solution is heating refluxed for 4 to 5 days. Next, the solution after heating reflux is filtered directly. The pH value of the above-mentioned solution of bis(3,4-dicarboxyphenoxy) compound (d) is adjusted to 2-3 by the hydrogen chloride solution. Therefore, initial product of solid 1,4-bis(3,4-dicarboxyphenoxy)-2-adamantyl benzene would be precipitated out. The solid 1,4-bis(3,4-dicarboxyphenoxy)-2-adamantyl benzene is washed several times by the distilled water and dried to obtain the final product.

The formation of 1,4-bis(3,4-dicarboxyphenoxy)-2-adamantyl benzene dianhydride comprises the following steps. Firstly, 1,4-bis(3,4-dicarboxyphenoxy)-2-adamantyl benzene obtained from the above-mentioned process, 30-40 ml of acetic anhydride, and excess acetic acid anhydride are added into the three-necked flask and heating refluxed at 130 to 140° C. The dehydrated ring-closure of the above-mentioned solution is carried out. 1,4-bis(3,4-dicarboxyphenoxy)-2-adamantyl benzene dianhydride 1.81 g is obtained after cooling down with 83.7% of the yield, and approximately 270-271° C. of the melting point. The property of 1,4-bis(3,4-dicarboxyphenoxy)-2-adamantyl benzene dianhydride is listed as below:

IR (KBr) 3068、2896、2850、1841、1771、1605、1474、1439 cm$^{-1}$; MS (EI) m/z 536 (M$^+$, 100), 478 (22).

The above-mentioned description is about the dianhydride monomer (e) provided in present invention. The polyimide compound (h) made by the above-mentioned dianhydride monomer (e) is introduced in the following paragraph. The general formula of polyimide compound (h) is shown as formula (VIII):

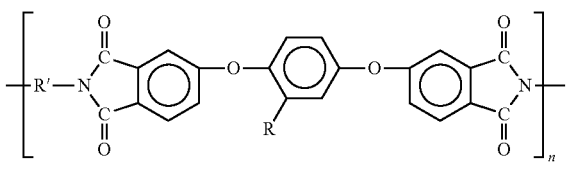

formula (VIII)

R' is selected from the group consisting of:

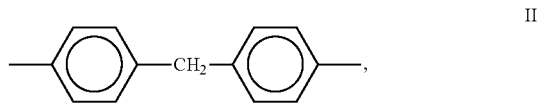

I

II

III

IV

V

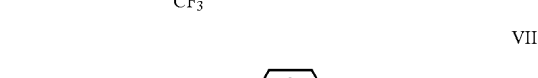

VI

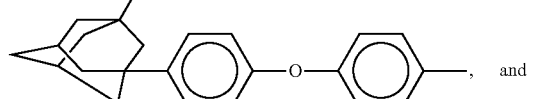

VII

, and

VIII

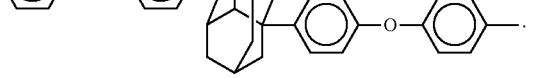

According to the above-mentioned formula of polyimide compound (h), polyimide compound (h) in the present invention has a large side chain. The large side chain would interrupt the symmetry of polyimide compound in structure and the regularity of polyimide compound in molecular arrangement.

Next, the manufacturing method of the polyimide compound (h) is introduced. The manufacturing method of polyimide compound (h) comprises the method of thermal imidization and chemical imidization. It is worth noting that, the "R'" mentioned hereafter is one of the above-mentioned eight groups cited as I to VIII and the detailed description of the eight functional groups would be omitted thereafter. The method of thermal imidization to manufacture the polyimide compound (h) would be introduced firstly. The method of thermal imidization comprises two main steps: forming polyamic acid compound (g) and forming polyimide compound (h).

The formation of polyamic acid compound (g) comprises the following steps. Firstly, diamine monomer (f) is dissolved in anhydrous N-methyl-2-pyrrolidone. The solution is stirred in an ice bath at 0-4° C. Then, dianhydride monomer (e) with same mole as the diamine monomer (1) is added and stirred for 1-2 hours. Next, the solution containing diamine monomer (f) and dianhydride monomer (e) is stirred at the room temperature for 4-5 hours to from polyamic acid compound (g). The general formula of the diamine monomer (f) is shown as formula (IX):

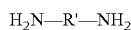   formula (IX)

The general formula of the polyamic acid compound (g) is shown as formula (X):

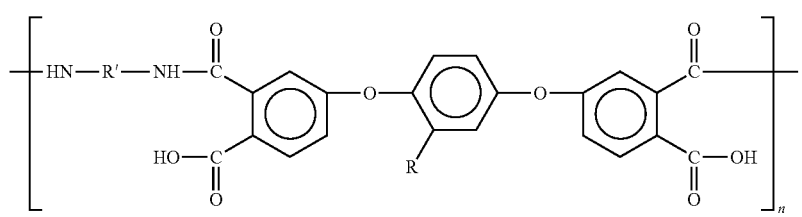

formula (X)

The formation of solid polyimide compound (h) comprises the following steps. The glass plate is (g) coated with the polyamic acid compound to form the film. Then, the glass plate is backed under vacuum at 100-300° C. Then, polyamic acid compound (g) is cyclized to form the solid polyimide compound (h) under the high temperature. The temperature of reaction is about 300-350° C. The general formula of the solid polyimide compound (h) is shown as formula (VIII):

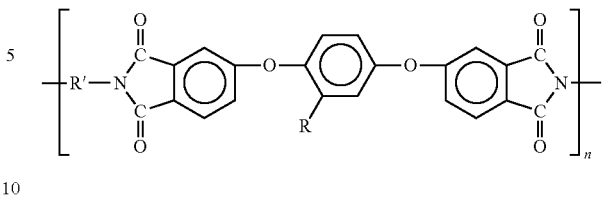

formula (VIII)

The dianhydride monomer (e) obtained from the first embodiment hereunder is reacted with one of the above-mentioned dianhydride monomers (f) to form polyimide compounds (h) by the method of thermal imidization as the second embodiment. However, the present invention is not limited thereto.

Second Embodiment 1,4-bis(3,4-dicarboxyphenoxy)-2-adamantyl benzene dianhydride is taken as the dianhydride monomer (e) of the polyimide in the second embodiment of the present invention. The functional group III is taken as the main chain of the diamine monomer (fIII). It is worth noting that the group III is the function group of the diamine monomer. Thus, the mark III would be added to the compound having function group III, such as diamine monomer (fIII), polyamic acid compound (g III), and polyimide (hIII). The formula of the polyimide (hIII) in the second embodiment of present invention is shown as formula (XI):

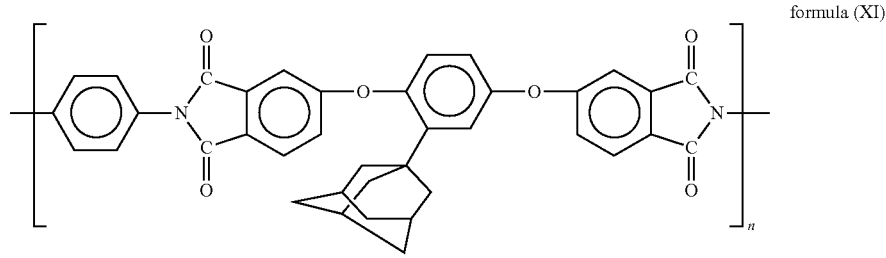

formula (XI)

It is worth noting that the thermal imidization to form polyimide (h III) has already been described as above and would be omitted thereafter.

The method of chemical imidization to manufacture the polyimide compound (h) is introduced next. The method of chemical imidization comprises three main steps: forming polyamic acid compound (g), forming liquid polyimide compound (h) and forming solid polyimide compound (h).

The formation of polyamic acid compound (g) comprises the following steps. Dianhydride monomer (e), diamine monomer (f) are dissolved into cresol with stirred under anhydrous condition to form polyamic acid compound (g). The reaction temperature is 20-30° C., and the reaction time is 6-7 hours.

Next, the formation of liquid polyimide compound (h) comprises the following steps. The 5-10 drops of isoquinoline are dropped into above-mentioned polyamic acid compound (g). The solution is heating refluxed at 100-200° C. or 8-12 hours, to form liquid polyimide compound (h). Herein, isoquinoline is used as dehydrating agent.

It is worth noting that, the step of forming polyimide compound (h) is a dehydrating step, and the process must be conducted under the anhydrous condition. In general, nitrogen or other inert gas would be introduced to avoid the influence of the moisture. In addition, cresol could be p-cresol or m-cresol, the present invention is not limited thereto. Furthermore, the heating reflux process of solution contained polyamic acid compound (f) and isoquinoline could be divided into three steps. Firstly, the solution is heating refluxed for 90-100° C. and for 2-4 hours. After that, the temperature of the reaction would be raised to 140-150° C. and the solution is heating fluxed for 2-4 hours. Next, the reaction temperature would be raised to 200-210° C. and the solution is heating fluxed for 2-4 hours.

Continued from the preceding paragraph, the above-mentioned solution of polyimide compound (h) is cooled to 20-30° C., and added into ethanol. Then, solid polyimide compound (h) is precipitated out. The solid polyimide compound (h) could be distilled by ethanol, and be obtained by the method of extraction to enhance the purity. The reaction temperature of the distillation is about 70-80° C. as the temperature of ethanol boiling point. The reaction time is 4-6 hours. Then, the solid polyimide compound (h) is obtained by the process of vacuum dried.

In order to further appreciate the contents of the present invention, the dianhydride monomer (e) obtained from the first embodiment hereunder is reacted with one of the above-mentioned dianhydride monomers (f) to from polyimide compounds (h) by the method of chemical imidization as the third to ninth embodiments. However, the present invention is not limited thereto.

Third Embodiment

In the third embodiment of present invention, 1,4-bis(3,4-dicarboxyphenoxy)-2-adamantyl benzene dianhydride as the dianhydride monomer (e) is reacted with diamine monomer (f I) having the function group I as the main chain. The formula of the polyimide (g I) in the third embodiment of present invention is shown as formula (XII):

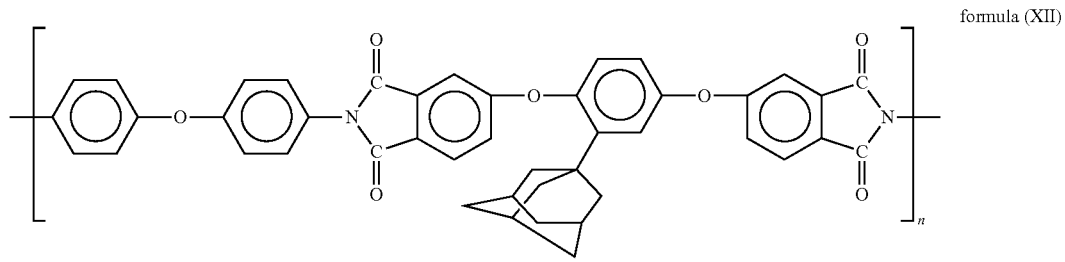

formula (XII)

It is worth noting that the method of chemical imidization utilized to form the polyimide (h I) have already described detailed as above and would be omitted thereafter. Befunctionals, the group I is the function group of the diamine monomer. Thus, the mark I would be added to the compound with function group I, such as diamine monomer (f I), polyamic acid compound (g I), and polyimide (h I). The function group II and function group IV to function group VIII would be mark as the same way in the following paragraph, and the description would be omitted thereafter.

Fourth Embodiment

In the fourth embodiment of present invention, 1,4-bis(3,4-dicarboxyphenoxy)-2-adamantyl benzene dianhydride as the dianhydride monomer (e) is reacted with diamine monomer (f II) having the function group II as the main chain. The formula of the polyimide (g II) in the third embodiment of present invention is shown as formula (XIII):

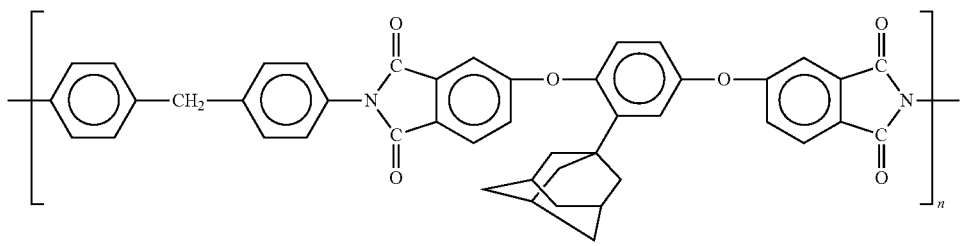

formula (XIII)

Fifth Embodiment

In the fifth embodiment of present invention, 1,4-bis(3,4-dicarboxyphenoxy)-2-adamantyl benzene dianhydride as the dianhydride monomer (e) is reacted with diamine monomer (fIV) having the function group IV as the main chain. The formula of the polyimide (h IV) in the third embodiment of present invention is shown as formula (XIV):

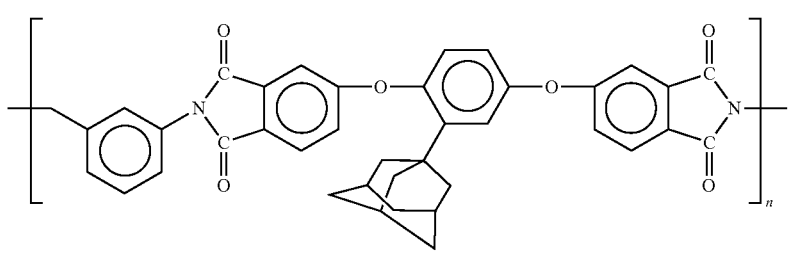

formula (XIV)

Sixth Embodiment

In the sixth embodiment of present invention, 1,4-bis(3,4-dicarboxyphenoxy)-2-adamantyl benzene dianhydride as the dianhydride monomer (e) is reacted with diamine monomer (fV) having the function group V as the main chain. The formula of the polyimide (hV) in the third embodiment of present invention is shown as formula (XV):

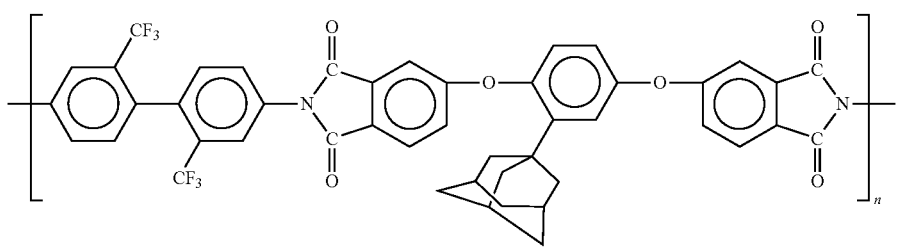

formula (XV)

Seventh Embodiment

In the seventh embodiment of present invention, 1,4-bis(3,4-dicarboxyphenoxy)-2-adamantyl benzene dianhydride as the dianhydride monomer (e) is reacted with diamine monomer (fVI) having the function group VI as the main chain. The formula of the polyimide (hVI) in the third embodiment of present invention is shown as formula (XVI):

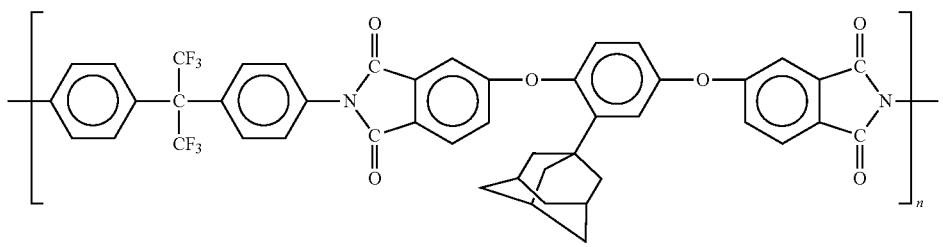

formula (XVI)

Eighth Embodiment

In the eighth embodiment of present invention, 1,4-bis(3,4-dicarboxyphenoxy)-2-adamantyl benzene dianhydride as the dianhydride monomer (e) is reacted with diamine monomer (fVII) having the function group VII as the main chain. The formula of the polyimide (hVII) in the third embodiment of present invention is shown as formula (XVII):

In the following paragraph, the analysis of the property of polyimide compounds in the second to ninth embodiment is conducted. The property comprises the viscosity test, the molecular weight test (such as the number average molecular weight Mn, average molecular weight Mw and polydispersity index Mw/Mn etc.), the solubility test, the mechanical property test (such as strength to break, elongation to break, and initial modulus etc.), and the thermal property test (such as

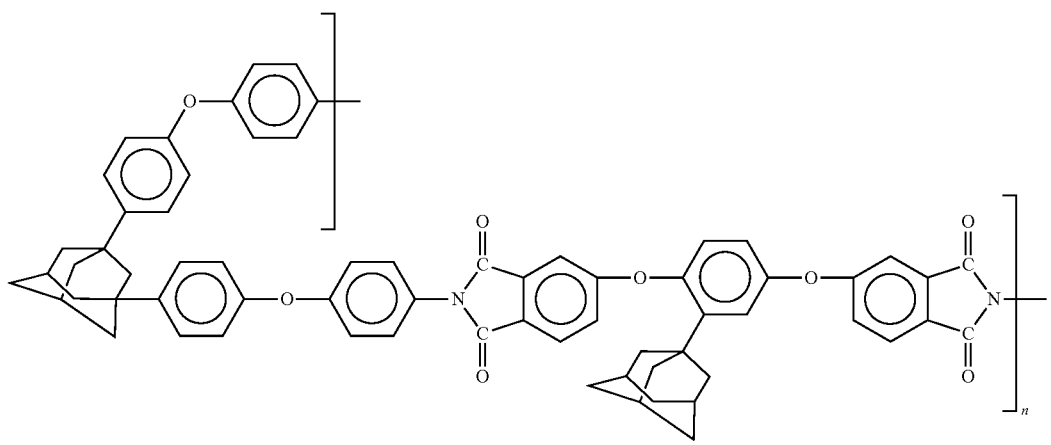

formula (XVII)

Ninth Embodiment

In the ninth embodiment of present invention, 1,4-bis(3,4-dicarboxyphenoxy)-2-adamantyl benzene dianhydride as the dianhydride monomer (e) is reacted with diamine monomer (fVIII) having the function group VIII as the main chain. The formula of the polyimide (h VIII) in the third embodiment of present invention is shown as formula (XVIII):

glass transition temperature Tg, the thermal degradation temperature in nitrogen, and the thermal degradation temperature in oxygen). Table 1 is the result of the viscosity test and the molecular test of polyimide (g' I to g'VIII, g" I to g"VIII). Table 2 is the result of solubility test of polyimide (g' I to g'VIII, g" I to g"VIII). Table 3 is the result of the mechanical property of polyimide (g" I to g"VIII). Table 4 is the result of the thermal property test of polyimide (g" I to g"VIII).

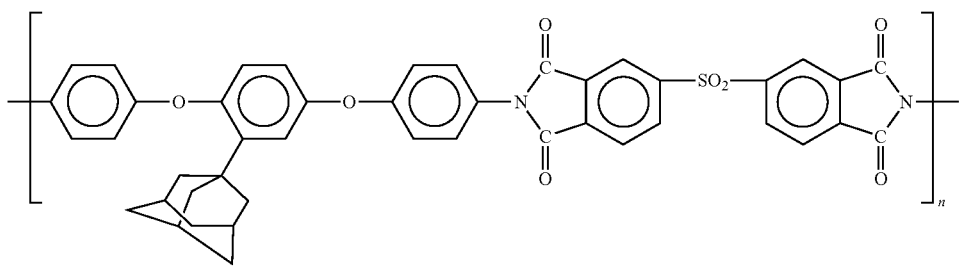

formula (XVIII)

TABLE 1

| | polyamic acid compound (g) | Polyimide compound(h) | | |
|---|---|---|---|---|
| | Viscosity $\eta_{inh}$(dL/g) | Mn × 10−4 | Mw/Mn | Viscosity $\eta_{inh}$(dL/g) |
| h I | — | 11.2 | 1.87 | 1.06 |
| h II | — | 7.9 | 1.89 | 0.54 |
| h III | 0.53 | — | — | — |
| h IV | — | 5.4 | 1.55 | 0.42 |
| h V | — | 10.6 | 1.67 | 0.44 |
| h VI | — | 7.1 | 1.92 | 0.47 |
| h VII | — | 7.7 | 1.64 | 0.69 |
| h VIII | — | 7.6 | 1.68 | 0.97 |

Please refer to the results shown in the Table 1. The viscosity of polyamic acid (g III) is in the range of 0.53 dL/g. The viscosity of solvable polyimide (h I, h II and hIV to hVIII) is in the range of 0.42 to 1.06 dL/g. The Mn of polyimide (h I to h III) is in the range of 42,000 to 112,000.

TABLE 2

| | NMP | DMAc | o-Chlorophenol | m-Cresol | Chloroform | THF |
|---|---|---|---|---|---|---|
| h I | +− | +− | + | ++ | ++ | +− |
| h II | ++ | − | ++ | ++ | ++ | − |
| h III | +− | − | +− | − | − | +− |
| h IV | ++ | +− | ++ | ++ | ++ | +− |
| h V | + | ++ | ++ | ++ | ++ | ++ |
| h VI | + | ++ | + | ++ | ++ | +− |
| h VII | + | +− | + | ++ | ++ | +− |
| h VIII | ++ | − | ++ | ++ | + | +− |

In the solubility test, N-methyl-2-pyrrolidone, N,N-dimethylacetamide (DMAc), o-chlorophenol, m-cresol, chloroform, and tetrahydrofuran are utilized to test the solubility of polyimide (g I to gVIII). The result of the solubility of the solubility is shown in Table 2. It's worth noting that, in Table 2, "++" refers to soluble at room temperature, "+" refers to soluble at 60° C., "+−" refers to partial soluble at 60° C., and "−" refers to insoluble at 60° C.

As the result shown in the Table 2, the main reason bring to the better solubility of polyimide (h V to h VI) in all kinds of solvent might be the group "—CF3" infunctional the polyimide (h V to h VI). The atom "F" is large, thus the arrangement between the molecular would be loose, and the solvent can be infiltrate into the molecular much easier. The solubility of polyimide (h V to h VI) would be enhanced.

Polyimide (hII) is made of ρ-phenylenediamine. The linear symmetry structure of ρ-phenylenediamine would make the tight arrangement between the molecular, and poor solubility of the compound. In addition, the polyimide (h I to h VIII) have good solubility in N-methyl-2-pyrrolidone, o-chlorophenol, m-cresol, and chloroform.

TABLE 3

| | Strength to Break (MPa) | Elongation to Break (%) | Initial Modulus (GPa) |
|---|---|---|---|
| h I | 114.7 | 20.7 | 2.2 |
| h II | 122.6 | 22.4 | 2.2 |
| h III | — | — | — |
| h IV | 141.6 | 8.3 | 2.4 |
| h V | 137.9 | 6.8 | 2.4 |
| h VI | 95.4 | 5.4 | 2.4 |
| h VII | 115.7 | 11.1 | 2.2 |
| h VIII | 117.8 | 10.5 | 2.2 |

Table 3 is the result of mechanical test of polyimide (h I to hIII). As the result shown in Table 3, the strength to break of polyimide (h I to h VIII) is in the range of 95.4 to 141.6 MPa. The elongation to break of polyimide (h I to hVI) is in the range of 5.4 to 22.4%. The initial modulus of polyimide (h I to hII) is in the range of 2.2 to 2.4 GPa. In addition, only the strength to break of the polyimide is less than 100 MPa, the other polyimide (hI to hIII, and hVII to hVIII) is higher than 110 MPa.

Polyimide (hI and hII) have the soften chain structure (such as —O— and —CH2-), thus the molecular curliness of the compound is high. The higher the molecular curliness, the greater the elongation of the polyimide. Therefore, the elongation to break of polyimide (hI and hII) is greater than 20%. On the other hand, although polyimide (hVII) also has the soften chain structure (—O—), the asymmetry 1,3-adamantanes in the main chain of polyimide (hVII) would decrease the elongation to break of the polyimide (hVII).

TABLE 4

| | DSC, Tg | Decomposition in N2 | Decomposition in Air |
|---|---|---|---|
| h I | 287 | 519 | 521 |
| h II | 287 | 510 | 508 |
| h III | 289 | 514 | 513 |
| h IV | 289 | 513 | 518 |
| h V | 280 | 507 | 515 |
| h VI | 297 | 509 | 507 |
| h VII | 268 | 529 | 534 |
| h VIII | 331 | 529 | 543 |

As the result shown in Table 4, the polyimide (h I to h VIII) have great property of heat resistance. In the nitrogen ambient, the main thermal degradation temperature is in the range of 507 to 529° C. In the air ambient, the main thermal degradation temperature is in the range of 507 to 543° C. According to the above-mentioned result, the polyimide (h I to hVIII) having aliphatic have greater property of thermal.

In addition, the analyzed result of DSC shows that the Tg of polyimide (h I to hIII) is in the range of 268 to 331° C. The strong structure of aliphatic group would cause the higher Tg of the polymer. The Tg of polyimide (h I to hVI) is around than 290° C. The Tg of polyimide (hVIII) even higher than 331° C. In addition, the lower Tg of polyimide (hVII) might be caused by the asymmetrical structure and several soft groups such as ether. The asymmetrical structure and several soft groups would decrease the intermolecular force and cause lower Tg.

To sum up, the present invention provides dianhydride monomer, polyimide compound and the manufacturing method thereof. The above-mentioned dianhydride monomer having large size of the functional group, thus the polyimide compound made of this kind of dianhydride monomer would have interrupted symmetry in structure and regularity in molecular arrangement. In addition, according to the result of the solubility test, the polyimide compounds having large size functional groups are soluble in various kinds of solvent. Furthermore, above-mentioned polyimide compounds can still maintain well mechanical and thermal property.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A dianhydride monomer having side chain, comprising the formula is listed as formula (I) below:

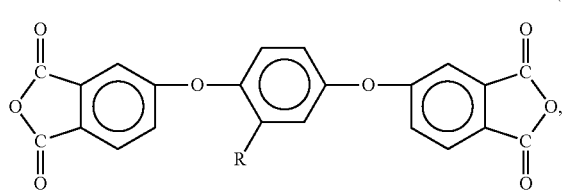

formula (I)

wherein R is a cycloalkane group with at least one tertiary carbon atom.

2. A manufacturing method of dianhydride monomer having side chain, comprising:

(A) heat refluxing the solution containing bromo compound (a), hydroquinone compound and benzene to separate out solid hydroquinone compound (b),
wherein the reaction temperature is 80-85° C., and the reaction time is 3-4 days,
wherein the formula of bromo compound (a) is shown as formula (II) below:

formula (II)

wherein the general formula of hydroquinone compound (b) is shown as formula (III) below

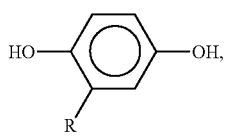

formula (III)

(B) heating the solution containing hydroquinone compound (b), and utilizing the methanol solution as the precipitant to form bis(3,4-dicyanophenoxy) compound (c),
wherein the reaction temperature is 75 to 80° C., and the reaction time is 6 to 12 hours,
wherein the general formula of bis(3,4-dicyanophenoxy) compound (c) is shown as formula (V) below:

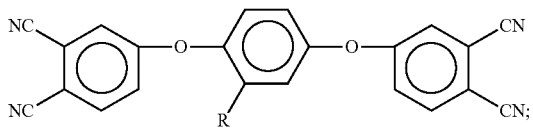

formula (V)

and (C) heating refluxing the solution containing bis(3,4-dicyanophenoxy) compound (c), potassium hydroxide, and methanol to separate out the solid bis(3,4-dicarboxyphenoxy) compound (d), wherein the reaction temperature is 70 to 85° C., and the reaction time is 4 to 5 days,
wherein the general formula of bis(3,4-dicarboxyphenoxy) compound (d) is shown as formula (VI) below

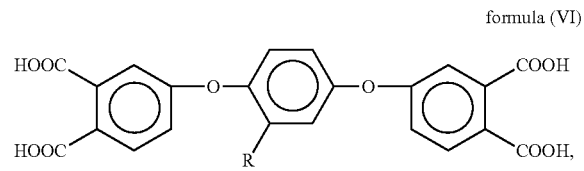

formula (VI)

(D) dehydrated ring-closuring the solution containing bis(3,4-dicarboxyphenoxy) compound (d), acetic anhydride, and acetic acid anhydride to form the dianhydride monomer (e),
wherein the reaction temperature is 130 to 140° C., and the reaction time is 1 to 6 days,
wherein the general formula of dianhydride monomer (e) is shown as formula (I) below:

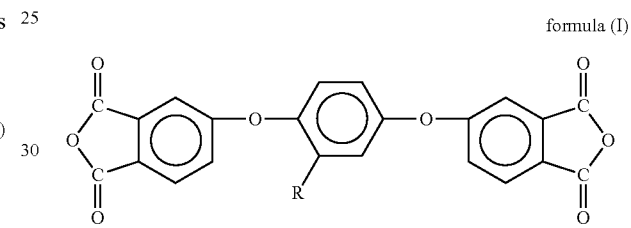

formula (I)

wherein R group is a cycloalkane group with at least one tertiary carbon atom.

3. The manufacturing method of dianhydride monomer having side chain of claim 2, wherein after the process of heating hydroquinone compound (b) and 4-nitrophthalonitrile further comprises:

heating refluxing the solution containing solid hydroquinone compound (b), potassium carbonate, toluene, and dimethylformamide, and hydroquinone compound (b) is dehydrated by the method of azeotrope to form the ionized hydroquinone having the anion,
wherein the temperature of azeotrope is about 150 to 160° C., and the reaction time is about 4 to 5 hours.

4. The manufacturing method of dianhydride monomer having side chain of claim 2, wherein the process after forming solid hydroquinone compound (b) further comprises:

washing solid hydroquinone compound (b) by the heating water,
wherein the temperature of heating water is 70 to 80° C.; and
recrystallizing solid hydroquinone compound (b).

5. The manufacturing method of dianhydride monomer having side chain of claim 2, wherein after the process of forming bis(3,4-dicyanophenoxy) compound (c) further comprises:

washing bis(3,4-dicyanophenoxy) compound (c) by the distilled water; and
recrystallizing the bis(3,4-dicyanophenoxy) compound (c).

6. A polyimide compound having side chain, comprising the formula is shown as formula (VIII) below:

formula (VIII)

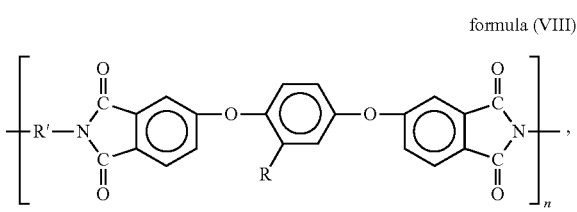

wherein R group is a cycloalkane group with at least one tertiary carbon atom, wherein R' is selected from the group consisting of:

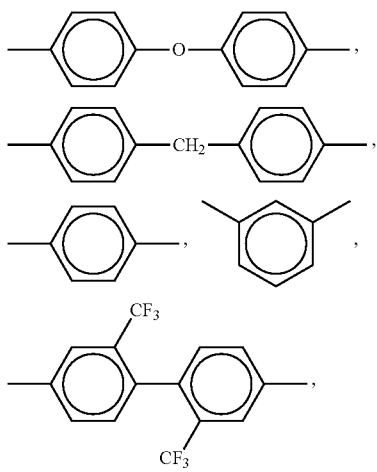

-continued

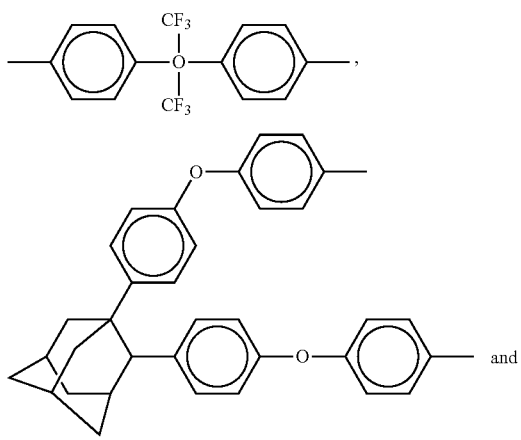

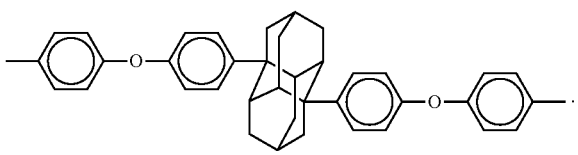

7. A manufacturing method of polyimide compound having side chain, comprising:

(A) dissolving dianhydride monomer, diamine monomer into cresol by stirring under anhydrous condition to form polyamic acid compound solution, wherein the general formula of dianhydride monomer is shown as formula (I) below:

Formula (I)

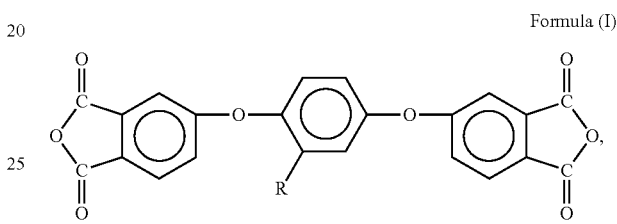

wherein the general formula of diamine monomer is shown as formula (IX) below:

$$H_2N-R'-NH_2$$ formula (IX), wherein the general formula of polyamic acid compound is shown as formula (X) below:

formula (X)

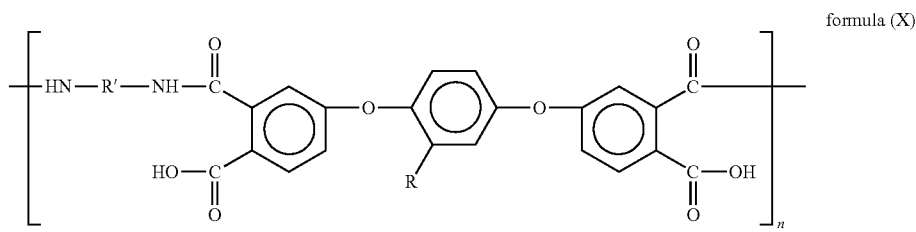

wherein R is a cycloalkane group with at least one tertiary carbon atom, wherein R' is selected from the group consisting of:

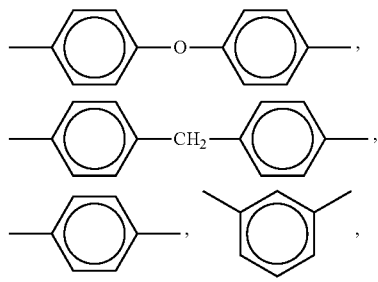

-continued

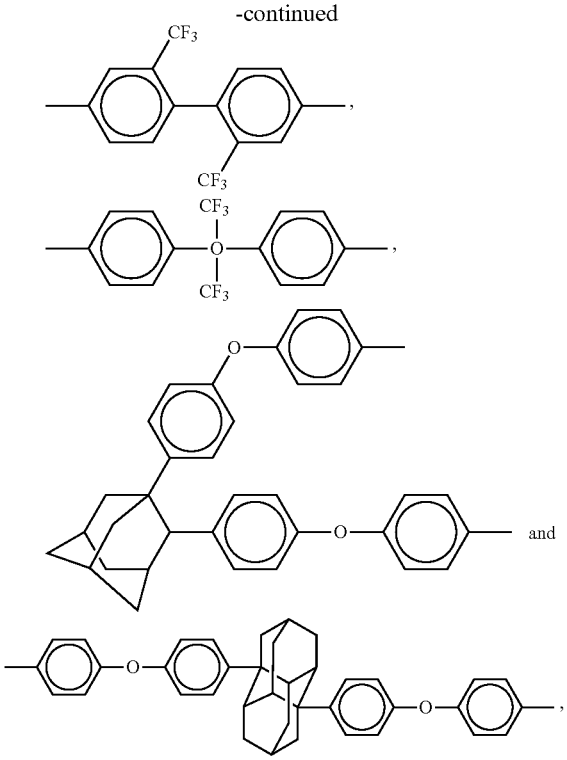
and wherein the reaction temperature is 20 to 30° C., the reaction time is 6 to 7 hours;
(B) adding 5-10 drops of isoquinoline to polyamic acid compound solution, and heating refluxing the solution to form polyimide compound solution,
wherein the reaction temperature is 100 to 200° C., the reaction time is 8 to 12 hours; and
(C) cooling polyimide compound solution and adding polyimide compound solution into ethanol to precipitate out solid polyimide compound, wherein the general formula of polyimide compound is shown as formula (VIII) below:

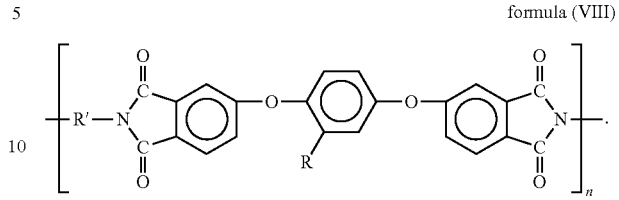

8. The manufacturing method of polyimide compound having side chain of claim 7, wherein cresol comprises p-cresol or m-cresol.

9. The manufacturing method of polyimide compound having side chain of claim 7, wherein after the process of forming the solid polyimide compound further comprises:
heating refluxing solid polyimide compound and ethanol, wherein the reaction temperature is 70 to 80° C., the reaction time is 4 to 6 hours.

10. The manufacturing method of polyimide compound having side chain of claim 7, wherein the process of heating refluxing the solution comprising polyamic acid compound and isoquinoline further comprises:
heating refluxing the solution comprising polyamic acid compound and isoquinoline for 90-100° C., wherein the reaction time is 2 to 4 hours;
raising the reaction temperature to 140-150° C. and heating refluxing the solution comprising polyamic acid compound and isoquinoline, wherein the reaction time is 2 to 4 hours; and
raising the reaction temperature to 200-210° C. and heating refluxing the solution comprising polyamic acid compound and isoquinoline, wherein the reaction time is 2 to 4 hours.

* * * * *